(12) United States Patent
Shippert

(10) Patent No.: US 6,517,509 B1
(45) Date of Patent: Feb. 11, 2003

(54) ABSORBENT PACK INSERTION INTO A HUMAN BODY CAVITY

(76) Inventor: Ronald D. Shippert, 4975 S. Albion St., Littleton, CO (US) 80121

( * ) Notice: Subject to any disclaimer, the term of this patent is extended or adjusted under 35 U.S.C. 154(b) by 0 days.

(21) Appl. No.: 09/496,883

(22) Filed: Feb. 2, 2000

(51) Int. Cl.[7] ............................................. A61F 13/20
(52) U.S. Cl. ........................................ 604/11; 604/904
(58) Field of Search ........................ 604/363, 11–18, 604/904, 57, 59–60; 606/196

(56) References Cited

U.S. PATENT DOCUMENTS

| | | | | |
|---|---|---|---|---|
| 1,969,671 A | * | 8/1934 | Nelson | 604/14 |
| 2,879,769 A | * | 3/1959 | Gordon et al. | 604/15 |
| 3,015,332 A | | 1/1962 | Brecht | 128/263 |
| 3,101,713 A | | 8/1963 | Sargent | 128/263 |
| 3,103,929 A | | 9/1963 | Brecht | 128/263 |
| 3,433,225 A | | 3/1969 | Voss et al. | 128/263 |
| 3,830,237 A | * | 8/1974 | Bernardin et al. | 604/359 |
| 4,030,504 A | | 6/1977 | Doyle | 128/325 |
| 4,088,132 A | * | 5/1978 | Wood et al. | 604/15 |
| 4,895,559 A | | 1/1990 | Shippert | 604/15 |
| 5,263,927 A | | 11/1993 | Shlain | 604/13 |
| 5,383,891 A | | 1/1995 | Walker | 606/196 |
| 5,395,309 A | | 3/1995 | Tanaka et al. | 604/18 |
| 5,445,605 A | * | 8/1995 | Pluss | 604/11 |
| 5,788,663 A | | 8/1998 | Igaue et al. | 604/15 |
| 5,817,047 A | * | 10/1998 | Osborn et al. | 604/14 |
| 5,827,215 A | | 10/1998 | Yoon | 604/15 |
| 6,071,259 A | * | 6/2000 | Steiger et al. | 604/11 |
| 6,177,608 B1 | * | 1/2001 | Weinstrauch | 604/380 |

* cited by examiner

*Primary Examiner*—Aaron J. Lewis
*Assistant Examiner*—C L Anderson
(74) *Attorney, Agent, or Firm*—Sheridan Ross P.C.

(57) ABSTRACT

A pack insertion device for use with a cavity in the human body, such as a nose cavity, is provided that includes an introducer member and a liquid absorption assembly. The introducer member is preferably one piece that can have a body member with side walls that form a rectangular cross-section. Alternatively, the introducer member is a single unit that includes a main body section and a pivotal body section that holds the liquid absorption assembly when positioned for insertion into a nasal or sinus cavity. In this embodiment, the introducer member has side walls that have cut-out portions, an intermediate wall that functions as a floor, and an elongated opening opposite the intermediate wall. In yet a further embodiment, the introducer member includes a single body having tapered side walls, an intermediate wall and an elongated opening opposite the intermediate wall. The liquid absorption assembly includes an absorbent member having a rectangular cross-section. The absorbent member further includes aproximal end, a distal end and a terminating section that optionally includes a cuff containing a marker to detect the location of the absorbent member when positioned in a nose cavity. The absorbent member is expelled into the nasal or sinus cavity by pulling the string member, while withdrawing the introducer member from the nasal opening.

18 Claims, 3 Drawing Sheets

FIG. 5
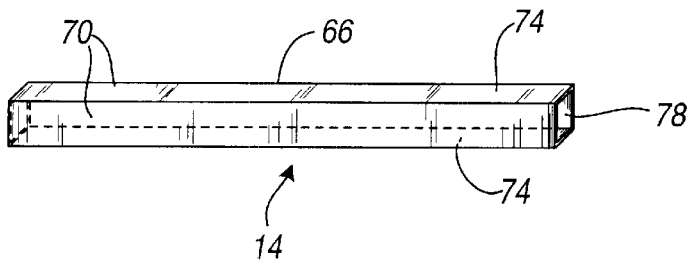
FIG. 6
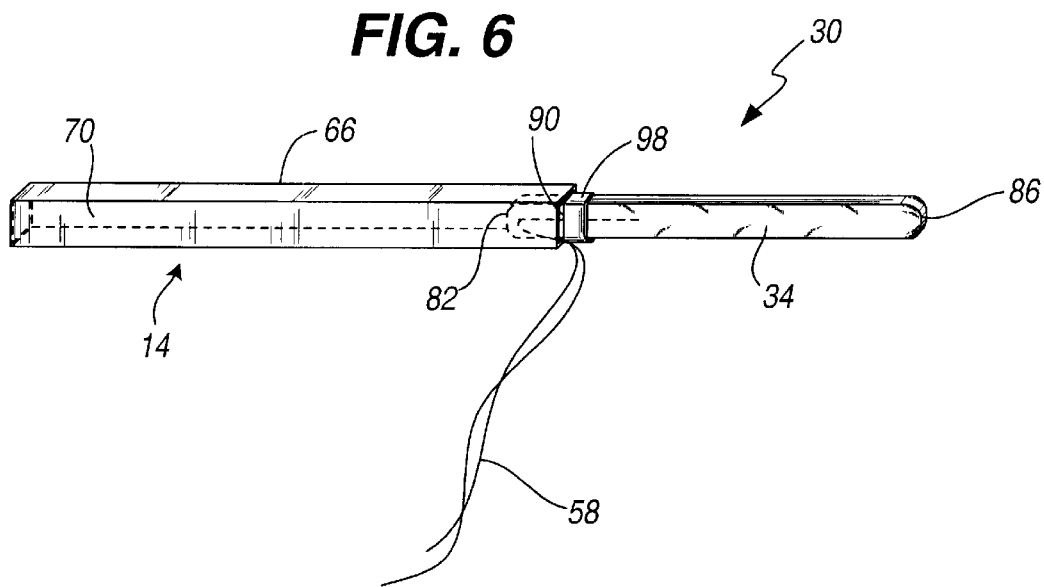
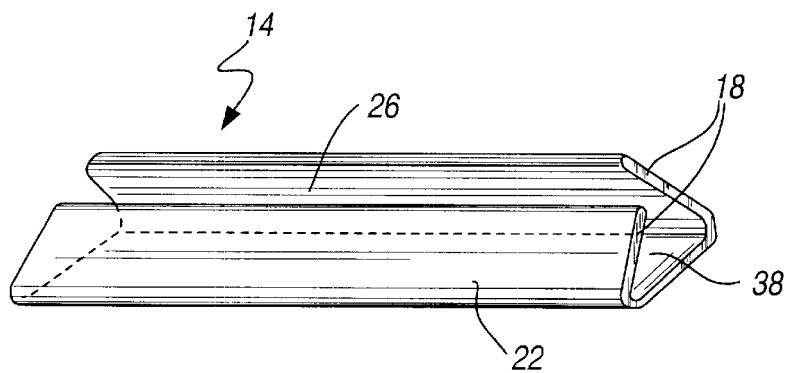
FIG. 7

ABSORBENT PACK INSERTION INTO A HUMAN BODY CAVITY

FIELD OF THE INVENTION

This invention relates to facilitating insertion of packing material into a cavity in the human body and, in particular, to treating nose hemorrhages.

BACKGROUND OF THE INVENTION

Nasal cavity or sinus cavity hemorrhaging is commonly treated by packing such a cavity with an absorbent foam material. The absorbent foam material serves two primary purposes. First, it absorbs the blood to prevent possible aspiration of the blood by the patient. Second, it averts the flow of blood by applying pressure to the ruptured blood vessel due to expansion of the absorbent foam material thereby acting as a hemostat.

At present, there are a number of devices that apply hemostatic pressure to control a hemorrhage in the nose and absorb blood associated with the hemorrhage. However, several of these devices require manual insertion of the absorbent material. For example, U.S. Pat. No. 4,030,504 to Doyle issued Jun. 21, 1977 and entitled "Nasal Hemostat and Method of Construction of Nasal Hemostat" uses an expandable absorbent material contoured to conform to the nasal cavity that must be inserted and positioned by hand.

Other known devices are typically formed or adapted at the time of use. For example, a physician will typically trim a piece of expandable absorbent material to the appropriate size, attach a suture to the absorbent material to facilitate retrieval, and manually insert the device into the patient's nasal or sinus cavity. The absorbent material then expands upon contact with blood. This expansion results in hemostatic pressure being applied to the ruptured blood vessel resulting in the arrest of blood flow. The absorbent material is then retrieved from the cavity by means of the attached suture.

Other body fluid-absorbing devices are also known. For example, catamenial devices that are used in a different application are described in U.S. Pat. No. 3,015,332 to Brecht issued Jan. 2, 1962 and entitled "Applicator," U.S. Pat. No. 3,103,929 to Brecht issued Sep. 17, 1963 and entitled "Catamenial Device," U.S. Pat. No. 3,101,713 to Sargent issued Aug. 27, 1963 and entitled "Tampon Applicator," and U.S. Pat. No. 3,433,225 to Voss issued Mar. 18, 1969 and entitled "Hygenic Devices and Methods of Making The Same." These catamenial devices, however, would be inappropriate for use in a nose cavity. For example, the absorbent material used in these catamenial devices is meant to merely absorb blood flow and is not meant to apply hemostatic pressure to stop blood flow. In addition, the circular cross section of the barrel and absorbent material used in the catamenial devices would be inappropriate for use in a nose cavity since the bone and cartilage structures of the cavity define a non-circular cross-section.

Therefore, these known nose and catamenial devices might require a significant amount of manual manipulation, may be time consuming to use, can result in a significant amount of patient discomfort, or are inappropriate for use in the nose. A syringe type applicator that inserts absorbent packing material into nose cavities has been developed by the inventor of the present invention to overcome the drawbacks associated with these other prior art devices. This syringe type device is disclosed in U.S. Pat. No. 4,895,559 to Shippert, issued Jan. 23, 1990 and entitled "Nasal Pack Syringe." However, this syringe type applicator may at times have difficulty expelling the packing material from the syringe, particularly when the contents are moisture sensitive causing the material to swell inside a syringe. Additionally, syringe type applicators can be more costly to make and assemble because of the number of parts.

Accordingly, a need exists for non-syringe type devices (i.e., no syringe plunger) that have fewer parts, are inexpensive to manufacture and can effectively insert an absorbent material into a human body cavity, including a hemorrhaging nose cavity that has a severely deviated canal, with a minimum amount of manual manipulation. The present invention satisfies such needs and provides related advantages.

SUMMARY OF THE INVENTION

The present invention provides an efficient, relatively painless and inexpensive way of delivering absorbent packing material to a patient's body cavity to absorb blood or other fluids and to apply hemostatic pressure to inhibit blood flow if present. The invention has a desirable containment feature in that contact with any blood that is present can be limited to the invention components and not spread to the operator or user thereof or elsewhere. The insertion device of the present invention can be characterized as having two components: (a) a single unit introducer member, and (b) a liquid absorption assembly.

The introducer member has a hollow volume and an outlet for the liquid absorption assembly to exit when expelled into the nasal or sinus cavity. In one embodiment, the hollow volume is closed in that it is defined by a single body member or shaft having two parallel wide sides and two parallel narrow sides to create a substantially rectangular cross section. The cross section defines the outlet, which is located at the distal end of the introducer member and is sized to hold the proximal end of the liquid absorption assembly securely in place until the absorbent member is expelled into the nose cavity as explained in more detail below. The walls are sufficiently strong (i.e. stiff) to hold the liquid absorption assembly in place. However, the narrow side walls can, but not necessarily, be made of thicker material than the wide side walls to provide a more solid platform for the absorbent member.

Alternatively, the introducer member has an open hollow volume defined by an elongated opening. In one embodiment, the introducer member includes a main body section and a pivotal body section formed by cut-out portions in the first and second side walls, an intermediate or connecting wall, and an elongated opening opposite the intermediate wall. In a further embodiment, the introducer member includes a single body having first and second side walls, an intermediate wall and an elongated opening opposite the intermediate wall without cut-out portions in the side walls.

The side and intermediate walls of the open volume embodiments are sufficiently strong to hold the liquid absorption assembly in place. However, the intermediate wall can, but not necessarily, be made of thicker material than the side walls to provide a more solid platform for the liquid absorption assembly as it is disengaged from the introducer member. In the embodiment having a pivotal body section, the intermediate wall beneath the cut-out portions is sufficiently flexible to allow pivotal movement of the pivotal body section relative to the main body section during the expulsion of the liquid absorption assembly into the nose cavity as explained in more detail below.

The elongated opening of the open volume embodiments has a length at least substantially corresponding to the lengths of the first and second side walls. The first and second side walls can be parallel or taper inwardly towards the elongated opening for a more secure holding of the liquid absorption assembly in the introducer member. Particularly in the embodiment in which the walls taper inwardly, different widths of absorption or packing material can be utilized in the same introducer member since such walls can be spread apart to accommodate reception of packing material of different widths. In addition, the height of the side walls of the introducer member can be lower than the height of the absorbent member to reduce the risk of cutting nose tissue and/or to make the introducer member less intrusive during the insertion process.

The introducer member is particularly useful when constructed of one piece and made of inexpensive disposable plastic material. The introducer can also be made of reusable plastic or metal materials.

The liquid absorption assembly includes an absorbent member having a proximal end, a distal end and a terminating section that is located closer to the proximal end than the distal end. A majority of the length of the absorbent member including the distal end extends exteriorly from the outlet of the introducer member when the introducer member and the absorbent member are positioned for inserting the absorbent member into a nose cavity, while the proximal end is held by the introducer member. In one embodiment, at least two-thirds of the length of the absorbent member, and preferably at least about eighty percent, extends exteriorly of the introducer member when the absorbent member is positioned for expelling into a nose cavity. The length of the absorbent member preferably extends from the nasal opening to the posterior margin of the turbinates and eustachian tube orifice.

The terminating section of the absorbent member can, but not necessarily, be of a first size that is larger than at least the size of the proximal end and can also be larger than the size of the distal end. The proximal end of the absorbent member is disposed in the hollow volume of the introducer member and exits from the outlet of the introducer member when the absorbent member is expelled into the nose cavity. The terminating section can also include a cuff having a marker for use in identifying the location of the absorbent member in the nose cavity, as well as in other parts of the human body when the absorbent member is inadvertently aspirated or swallowed. In the embodiment of the introducer member having a pivotal body and main body sections, the terminating section is located adjacent to the cutout portions of the introducer member. In the embodiment without cut-out portions, the terminating section lies outside and adjacent to the outlet of the introducer member.

The absorbent member can be made of any material capable of expanding as it absorbs blood or other fluids. Preferably, the absorbent member can be compressed in at least two directions prior to use.

The liquid absorption assembly includes a string member, which when pulled expels the absorbent member from the introducer member into the nose cavity. The string member can be attached to the proximal end or terminating section of the absorbent member. Alternatively, the string member can be attached to a portion or throughout the length of the absorbent member (for example, sewn down the length of the absorbent member) and can extend from the absorbent member either from the proximal or distal end. Once the absorbent member is properly positioned in a nose cavity, the string member can be secured externally of the cavity, for example, taped to the patient's face to assist in the prevention of aspiration or swallowing of the absorbent member. Preferably, the string member forms a loop that can be secured by wrapping the loop around an ear of the patient. After the absorbent material has served its purpose, it can be removed from the nose cavity by pulling the string member out the nasal opening.

The present invention further provides methods for inserting an absorbent member into a nose cavity. The methods are generally accomplished by:

(a) providing an introducer member holding an absorbent member, wherein the absorbent member is attached to a string member;

(b) positioning the absorbent member in a cavity located in a nose; and (c) expelling the absorbent member from the introducer member into the cavity using the string member.

In one embodiment, the introducer member has a pivotal body section which is pivoted during the expulsion of the absorbent member from the introducer member by the string member. In this embodiment, pulling on the string member will bend the intermediate wall beneath the cut-out portions of the introducer member causing the main body section of the introducer to pivot downward relative to the pivotal body section, which facilitates the removal of the pivotal body section out the nasal opening while expelling the absorbent member into the desired nose cavity. In an alternative embodiment, the introducer member has a single body with the side walls that are parallel or tapered toward an elongated opening. In both embodiments, the absorbent member preferably extends above the elongated opening to reduce the risk of tissue damage.

In yet another embodiment, the introducer member has a single body member or single shaft such that pulling on the string member facilitates the removal of the shaft tip out the nasal opening while expelling the absorbent member into the nose cavity.

The methods of the present invention further comprise the step of connecting a portion of the string member on or adjacent to a patient's face to avoid, after the absorbent member is positioned in the nose cavity, aspiration of the absorbent member. For example, the string member can be taped to a patient's face. Alternatively, the string member can be in the form of a loop wrapped around the patient's ear. Once the absorbent member has served its purpose, it can be withdrawn from the nose cavity by pulling on the attached string member.

Based on the foregoing summary, a number of salient features of the present invention are recognized. A foam pack device is provided having a reduced number of parts for absorbing blood and applying pressure in a human body cavity after expansion of the foam packet. Although the application of the present invention with a nose cavity is described, other cavities in the human body are applicable including ear cavities, appropriate tissue-formed cavities and the vagina. The device also functions to contain blood so that unwanted contact and spreading thereof are avoided.

Additional advantages of the present invention will become readily apparent from the following description when taken in conjunction with the accompanying drawings.

BRIEF DESCRIPTION OF THE DRAWINGS

FIG. 5 is a side view of an introducer member having a single body member or shaft.

FIG. 6 is a side view of the introducer member of FIG. 6 holding a liquid absorption assembly in a ready position for inserting into a nasal cavity.

FIG. 7 is a side view of an introducer member having a single body without cut-out portions and having side walls that taper toward the elongated opening.

DETAILED DESCRIPTION

Figure 1:
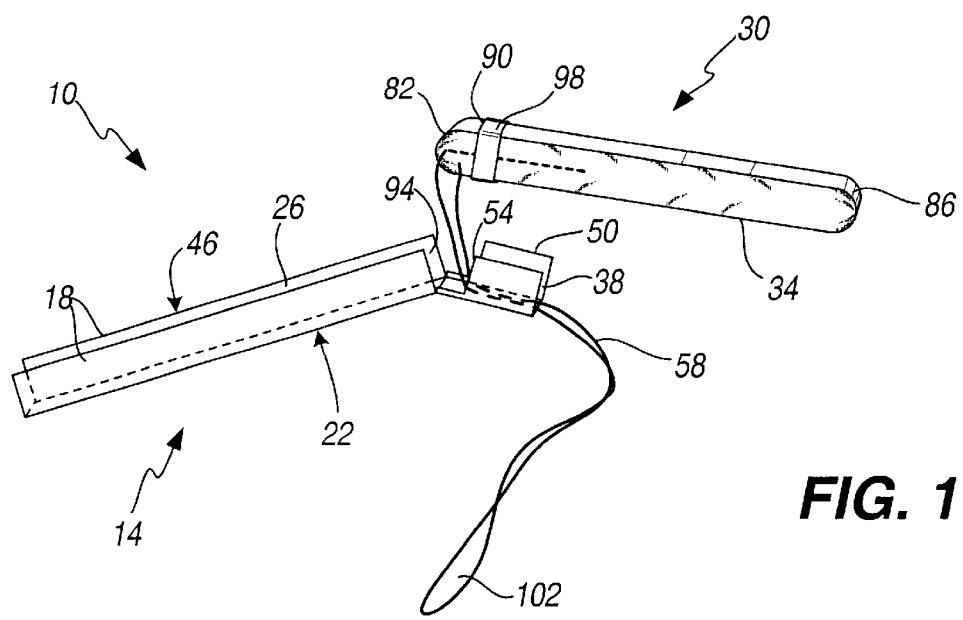
FIG. 1 is an exploded view of an introducer member and a liquid absorption assembly in which the cut-out portion is shown in the bent position.

The present invention relates to novel nose pack insertion devices used to absorb blood and other fluids from nasal and/or sinus cavities and, if needed, to function as a hemostat in the cavity. These devices include two main components: (a) a single unit introducer member, and (b) a liquid absorption assembly.

With reference to the nose pack insertion devices 10 illustrated in FIGS. 1–4 and 7, the single unit introducer member 14 includes two side walls 18, an intermediate wall 22 and an elongated opening 26 opposite the intermediate wall 22. The total length of the introducer member 14 should be sufficiently long to hold the liquid absorption assembly 30 in place while positioning the liquid absorption assembly 30 into a nose cavity. In addition, the length of the introducer member 14 can be customized to hold a liquid absorption assembly 30 that will fit into a nose cavity of a particular patient. Accordingly, the elongated opening 26 has a length at least substantially corresponding to the lengths of the first and second side walls 18.

Figure 3:
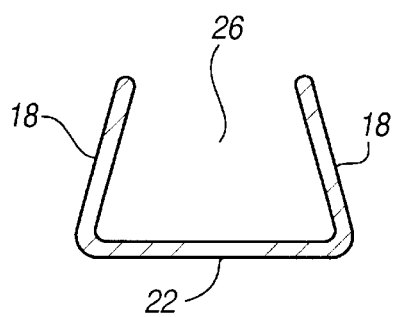
FIG. 3 is an end view of the pivotal section showing the two side walls tapering toward the elongated opening.

The first and second side walls 18 can be parallel or taper inwardly towards the elongated opening 26 for a more secure holding of the liquid absorption assembly 30 in the introducer member 14 as shown in FIGS. 3 and 7. In addition, the height of the side walls 18 can be lower than the height of the absorbent member 34 to minimize the risk of cutting nose tissue and/or to make the introducer member 14 less intrusive during the insertion process.

The side walls 18 and the intermediate wall 22 are sufficiently strong to hold the liquid absorption assembly 30. In one embodiment, the intermediate wall 22 is thicker than the side walls 18 to provide a more solid foundation for the absorbent member 34 as it exits the outlet 38 of the introducer member 14.

Figure 2:
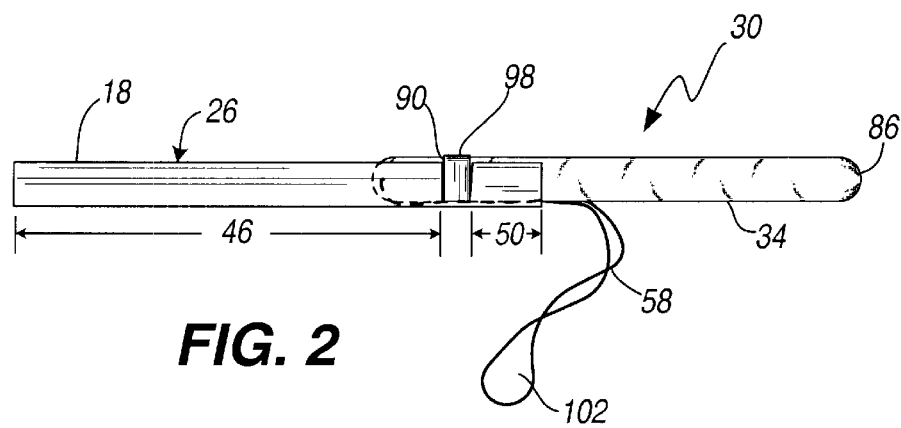
FIG. 2 is a side view of the introducer member of FIG. 1 holding the liquid absorption assembly in a ready position for inserting into a nasal cavity.
Figure 4:
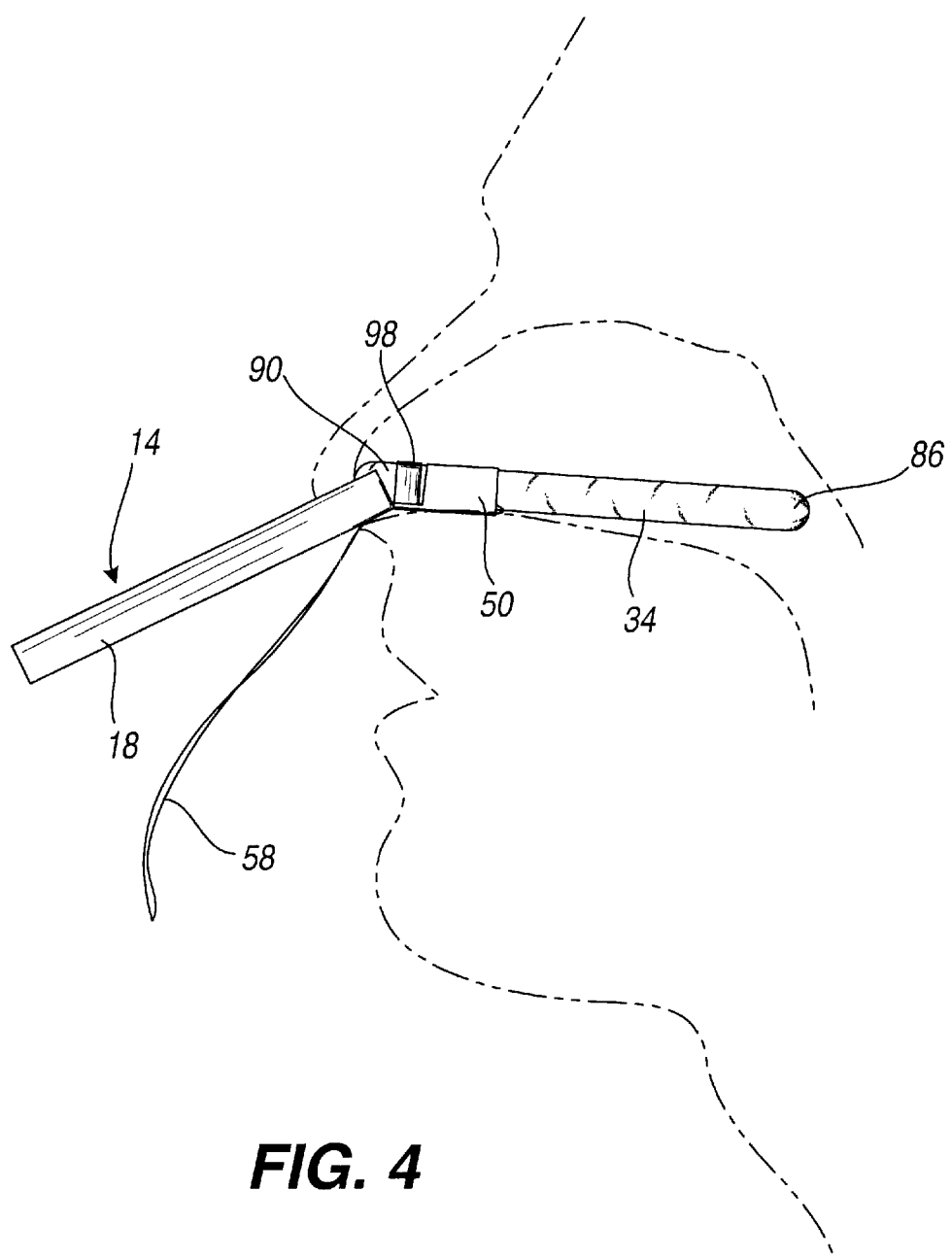
FIG. 4 illustrates the insertion of the absorbent material into a nasal cavity using the introducer member of FIG. 1.

With reference to the nose pack insertion device 10 illustrated in FIGS. 1, 2 and 4, the first and second side walls 18 of the introducer member 14 each contain a cut-out portion 42 to form a main body section 46 and a pivotal body section 50. In one embodiment, the first and second side walls 18 of the pivotal body section 50 have an angled cut 54 on the side adjacent to the cut-out portions 42 as best shown in FIG. 1. The angled cut 54 can form an acute angle relative to the elongated opening 25. In one embodiment, the acute angle 54 is in a range between about 50° to about 80°, and preferably about 60°.

With continued reference to the introducer member 14 of FIGS. 1, 2 and 4, the intermediate wall 22 is sufficiently flexible to rotate the pivotal body section 50 relative to the main body section 46 when the string member 58 is pulled to expel the absorbent member 34 into the nose cavity. In one embodiment, the flexibility of the intermediate wall 22 can be attributed to a hingle-like section 62 joining the intermediate wall 22 of the main body section 46 to the intermediate wall 22 of the cut out portions 42 as best seen in FIG. 1.

In one embodiment, the side walls 18 of the introducer member 14 have a thickness less than the thickness of the intermediate wall 22 The height of the introducer member 14 is about 0.28 inch±0.060 inch. The length of the elongated opening 26 formed by the main body section 46 is about 3.20 inch±1 inch and the length of the elongated opening 38 formed by the pivotal body section 50 is about 0.2 inch±0.050 inch. The width of the elongated opening 26 is about 0.2 inch±0.020 inch when the side walls 18 are parallel and about 0.05 inch±0.010 inch when the side walls 18 are tapered.

In an alternative embodiment as shown in FIGS. 5 and 6, the introducer member 14 comprises a shaft 66 having two parallel wide sides 70 that are integrally connected by means of two parallel narrow sides 74. The wide and narrow sides 70, 74 of the shaft 66 form a substantially rectangular cross-section that defines a closed hollow volume. The shaft 66 also includes an outlet 78 from which the proximal end 82 of the absorbent member 34 exits when expelled into a nose cavity.

The introducer member 14 has a sufficient length so that it can be held while manipulating the absorbent member 34 into a nose cavity of a patient. In addition, the introducer member 14 can be of sufficient length to house a substantial portion of the liquid absorption assembly 30 during storage. The liquid absorption assembly 30 can then be positioned as shown in FIG. 6 just prior to use. Those skilled in the art can readily determine an appropriate length for such purposes.

The introducer members of the present invention are preferably made of inexpensive plastic material. Particularly useful disposable, inexpensive plastics include, for example, polypropylene and the like. When a non-disposable embodiment of an introducer member is desired, other materials can be utilized, such as more durable or reuseable plastic materials, or even non-plastic materials that might include one or more metals. Alternatively, a combination of materials can be used to construct the introducer member if desired. Preferably, however, the introducer member is constructed in one piece by any appropriate method known in the art, including, for example, by extrusion or molding. All dimensions disclosed herein for the introducer members relate to the finished product, including, for example, after heat treatment.

The liquid absorption assembly 30, as shown in FIGS. 1, 2, 4, 6 and 7, includes an absorbent member 34, a proximal end 82, a distal end 86 and a terminating section 90, which is closer to the proximal end 82 than the distal end 86. As best shown in FIGS. 2, 6 and 7, the majority of the absorbent member 34, including the distal end 86, extends exteriorly from the outlet 38 of the introducer member 14, while the proximal end 82 is engaged (i.e., held) within the introducer member 14 when the absorbent member 34 is positioned for insertion into a nose cavity. In one embodiment, at least two-thirds, and preferably at least 80%, of the absorbent member 34 extends exteriorly of the introducer member 14 when the absorbent member 34 is positioned for insertion into a nose cavity. FIGS. 2 and 6 further show the engagement of the absorbent member 34 by the introducer member 14 in which the proximal end 82 is disposed in the hollow volume of the introducer member 14 (FIG. 6) or the outlet 94 of the main body section 46 (FIG. 2).

The terminating section 90 may have a size (e.g. width) that is larger than the proximal end 82 and can further have a size (e.g. width) that is larger than the distal end 86. As shown in FIG. 7, the terminating section 90 of the absorbent member 34 lies adjacent to and exteriorly of the outlet 38 of the introducer member 14. Alternatively, the terminating section 90 can be located adjacent to the cutout portions 42 of the introducer member 14 as shown in FIG. 1.

The terminating section 90 can also include a cuff 98 having a marker for use in identifying the location of the absorbent member in the nasal cavity. The cuff 98 can be made of any material in which a marker can be imbedded, sewn or otherwise placed in or on the material so the marker is detectable. Those skilled in the art can readily identify appropriate markers and methods of making cuffs having such markers. Particularly useful markers include, for example, radiopaque markers such as barium sulfate, which can be detected by x-ray.

The absorbent member can be made of any material capable of expanding as it absorbs blood or other fluids. Those skilled in the art can readily identify suitable materials for use as the absorbent member including, for example, foam, such as PVA foam. Preferably, the absorbent member can be compressed in at least two directions prior to use. Methods of making the absorbent material in a desired shape and size to fit a nasal or sinus cavity are known to those skilled in the art.

The liquid absorption assembly 14 preferably includes a string member 58, which when pulled expels the absorbent member 34 from the introducer member 14 into the nose cavity. The string member 58 can be attached to the proximal end 82, distal end 86, or terminating section 90 of the absorbent member 34 and is fed from the introducer member 14 as best shown in FIG. 1. Alternatively, the string member 58 can be attached throughout the length or a portion of the absorbent member 34 (for example, sewn down the length of the absorbent member) and extends from the absorbent member 34 either from the proximal end 82 or distal end 86. It has been observed that, when the string member 58 is attached to the absorbent member 34 along its complete length, more rapid absorption of blood or other fluids occurs. It appears that the string member 58, together with the holes formed in the absorbent member when the string member 58 is stitched thereto, create additional pathways to the center of the absorbent member 34 whereby a more direct route is provided to the center or other inner portions of the absorbent member 34. Once the absorbent member 34 is properly positioned in the desired nose cavity, the string member 58 can be secured externally of the cavity, for example, taped to the patient's face. Preferably, the string member 58 forms a loop 102 that extends from the absorbent member 34 so the string member 58 can be secured by wrapping the loop 102 around an ear of the patient. After the absorbent member 34 has served its purpose, it can be removed from the nasal cavity by pulling the string member 58 out the nasal opening. The string member can be made of any suitable material used in medical applications, including, for example, sutures. In addition, the string member is of a length to permit ready attachment of the string member to the exterior of a patient's nasal cavity as described above.

The present invention further provides methods for using the novel nose pack insertion devices. The methods include the steps of:

(a) providing an introducer member holding an absorbent member, wherein the absorbent member is attached to a string member;

(b) positioning the absorbent member in a nose cavity; and (c) expelling the absorbent member from the introducer member into the cavity using the string member.

In one embodiment best illustrated by FIG. 4, the introducer member 14 has a pivotal body section 50 which is pivoted during the expulsion of the absorbent member 34 from the introducer member 14 by the string member 58. In this embodiment, a user pulls on the string member 58 which will bend the intermediate wall 22 beneath the cut-out portions 42 of the introducer member causing the main body section 46 of the introducer member 14 to pivot downward relative to the pivotal body section 50. Pivoting facilitates the removal of the pivotal body section 50 out the nasal opening, while freeing and expelling the absorbent member 34 into a nose cavity. In this embodiment, the absorbent member 34 preferably extends above the elongated opening 26 to reduce the risk of tissue damage and/or minimize discomfort to the patient during the insertion process.

In an alternative embodiment as best shown in FIG. 6, the introducer member 14 has a single shaft 66 such that pulling on the string member 58 facilitates the removal of the shaft outlet 78 out the nasal opening, while simultaneously freeing and expelling the absorbent member 34 into the nasal cavity.

In all embodiments, a majority of the length of the absorbent member 34 is located outside the introducer member 14 when the introducer member 14 holds the absorbent member 34 in position for inserting into a nasal cavity. Preferably, at least two-thirds of the length of the absorbent member 34, and more preferably about 80% extends exteriorly of the introducer member 14 while holding the absorbent member 34 prior to insertion.

The methods of the present invention further comprise the step of connecting a portion of the string member 58 on or adjacent to a patient's face before or after the absorbent member 34 is expelled into a nose cavity. For example, the string member 58 can be taped to a patient's face. Alternatively, the string member 58 can be in the form of a loop 102 wrapped around the patient's ear. Once the absorbent member 34 has served its purpose, it can be withdrawn from the cavity by pulling on the attached string member 58.

While the devices and methods described herein constitute the preferred embodiments of the invention, it is to be understood that the invention is not limited to these embodiments and that changes can be made without departing from the scope of the invention as defined in the claims.

What is claimed is:

1. A device engaged by a user for use with a cavity in the human body, comprising:

an introducer member having a hollow volume and an outlet, said introducer member including a body having first and second side walls, an intermediate wall and an elongated opening opposite said intermediate wall, portions of said first and second side walls, said intermediate wall and said elongated opening being part of a main body section and other portions of said first and second side walls, said intermediate wall and said elongated opening being part of a pivotal body section, with cut-out portions being located between said main body section and said pivotal body section; and a liquid absorption assembly including an absorbent member having a length and including a proximal end and a distal end, wherein a majority of said length of said absorbent member including said distal end extends exteriorly from said introducer member when said introducer member and said absorbent member are positioned for inserting said absorbent member into the cavity while said proximal end is held by said introducer member, said liquid absorption assembly further including a string member that is used to expel said absorbent member into the cavity by the user pulling on said string member and with no pushing on said absorbent member while said string member is being pulled.

2. A device, as claimed in claim 1, wherein:
said liquid absorption assembly includes a terminating section having a width and said proximal end has a width, said terminating section width being greater than said proximal end width, with said proximal end being disposed in said hollow volume of said introducer member and exiting said introducer member through said outlet when said absorbent member is expelled into the cavity.

3. A device, as claimed in claim 1, wherein:
said liquid absorption assembly includes a terminating section that includes a cuff member having a marker for use in identifying a location of said absorbent member in the cavity, said cuff member being different than each of said string member and said absorbent member.

4. A device, as claimed in claim 1, wherein:
at least two-thirds of said length of said absorbent member extends exteriorly of said introducer member when said introducer member and said absorbent member are positioned for expelling said absorbent member into the cavity.

5. A device, as claimed in claim 1, wherein:
said string member has portions that can be connected externally of the cavity.

6. A device, as claimed in claim 1, wherein:
said string member forms a loop capable of wrapping around an ear.

7. A device, as claimed in claim 1, wherein:
said absorbent member is foam.

8. A device, as claimed in claim 1, wherein:
said liquid absorption assembly includes a terminating section that is located adjacent to said cut-out portions of said introducer member.

9. A device, as claimed in claim 1, wherein:
said cut-out portions enable pivotal movement of said pivotal body section during expulsion of said absorbent member from said introducer member into the cavity.

10. A device for use with a cavity in the human body, comprising:
an introducer member including a body having a hollow volume, an outlet, first and second side walls, an intermediate wall, and an elongated opening opposite said intermediate wall, with said first and second side walls tapering inwardly towards said elongated opening; and
a liquid absorption assembly including an absorbent member having a length and including a proximal end, a distal end and a terminating section that is located closer to said proximal end than to said distal end, wherein a majority of said length of said absorbent member including said distal end extends exteriorly from said introducer member when said introducer member and said absorbent member are positioned for inserting said absorbent member into the cavity while said proximal end is held by said introducer member.

11. A device for use with a cavity in a human body, comprising:
an introducer member including a body having first and second side walls, an intermediate wall, and an elongated opening opposite said intermediate wall, portions of said first and second side walls, said intermediate wall and said elongated opening being part of a main body section and other portions of said first and second side walls, said intermediate wall and said elongated opening being part of a pivotal body section, with cut-out portions being located between said main body section and said pivotal body section; and
a liquid absorption assembly including an absorbent member held by said introducer member for insertion into the cavity and a string member that is positioned for use in causing pivotal movement of said pivotal body section and thereby insertion of said absorbent member into the cavity.

12. A device for use with a cavity in a human body, comprising:
an introducer member including a body having first and second side walls, an intermediate wall, and an elongated opening opposite said intermediate wall that has a length at least substantially corresponding to lengths of said first and second side walls, portions of said first and second side walls, said intermediate wall and said elongated opening being part of a main body section and other portions of said first and second side walls, said intermediate wall and said elongated opening being part of a pivotal body section, with cut-out portions being located between said main body section and said pivotal body section; and
a liquid absorption assembly including an absorbent member held by said introducer member for insertion into the cavity.

13. A device, as claimed in claim 11, wherein:
said absorbent member includes a distal end, a proximal end and a terminating section located between said distal end and said proximal end, with said terminating section being of a different size than each of said distal end and said proximal end.

14. A device, as claimed in claim 11, wherein:
said absorbent member has a length, with less than a majority of said length of said absorbent member being located interiorly of said introducer member when said introducer member and said absorbent member are being positioned in the cavity.

15. A method for inserting an absorbent member into a cavity in a human body, comprising:
providing an introducer member holding the absorbent member, said absorbent member having a string member attached thereto;
positioning said absorbent member in a cavity;
engaging said string member by a user; and
expelling said absorbent member from the introducer member into the cavity by said string member being pulled by the user, said expelling step including starting said expelling by said string member being pulled by the user; and
connecting a portion of said string member adjacent to a body part in the proximity of the cavity after said expelling step.

16. A method for inserting an absorbent member into a cavity in a human body, comprising:
providing an introducer member holding the absorbent member, said introducer member including first and second side walls, an intermediate wall and an elongated opening opposite said intermediate wall, and said absorbent member extends above said elongated opening, said absorbent member having a string member attached thereto;

positioning said absorbent member in a cavity; and expelling said absorbent member from the introducer member into the cavity using said string member.

17. A method, as claimed in claim 15, wherein:

said expelling step is conducted free of pushing on said absorbent member.

18. A method for inserting an absorbent member into a cavity in a human body, comprising:

providing an introducer member holding the absorbent member, said absorbent member having a string member attached thereto, said introducer member having a pivotal body section;

positioning said absorbent member in a cavity; and expelling said absorbent member from the introducer member into the cavity using said string member, said expelling step including pivoting said pivotal body section using said string member.

* * * * *